United States Patent [19]

Black et al.

[11] Patent Number: 5,163,935

[45] Date of Patent: Nov. 17, 1992

[54] SURGICAL LASER ENDOSCOPIC FOCUSING GUIDE WITH AN OPTICAL FIBER LINK

[75] Inventors: Michael Black, Foster City; Vladimir Kupershmidt, Fremont, both of Calif.

[73] Assignee: Reliant Laser Corporation, Foster City, Calif.

[21] Appl. No.: 658,343

[22] Filed: Feb. 20, 1991

[51] Int. Cl.[5] .............................................. A61N 5/06
[52] U.S. Cl. .......................................... 606/17; 128/4; 606/7; 606/15; 606/16
[58] Field of Search ....................... 606/2, 3, 7, 10-18; 128/4, 6, 397, 398

[56] References Cited

U.S. PATENT DOCUMENTS

| | | | |
|---|---|---|---|
| 4,740,047 | 4/1988 | Abe et al. | 128/4 X |
| 4,760,840 | 8/1988 | Fournier, Jr. et al. | 606/16 X |
| 4,865,029 | 9/1989 | Pankratov et al. | 606/7 X |
| 5,002,042 | 3/1991 | Okada | 128/6 |
| 5,041,121 | 8/1991 | Wondaazek et al. | 606/15 X |
| 5,078,711 | 1/1992 | Kakami et al. | 606/15 X |

*Primary Examiner*—Peter A. Aschenbrenner
*Attorney, Agent, or Firm*—David Pressman

[57] ABSTRACT

A surgical laser endoscopic focusing guide for a laser fiber optical link comprises a disposable unit (14) which is connected to the end of an optical fiber link (10). The unit consists of an endoscopic tube (16), the front end of which contains a mirror lens (22) for directing a laser beam emitted from the unit onto the operation area. The lens (22) bends the beam in a lateral direction onto a tissue to be treated. In an embodiment for laser angioplasty, the unit has a firm and reliable attachment directly to a buffer layer (80) of the optical fiber link. This ensures flexibility required for operaton in narrow and curved vessels and provides firm attachment of the mirror lens to the tube.

8 Claims, 2 Drawing Sheets

SURGICAL LASER ENDOSCOPIC FOCUSING GUIDE WITH AN OPTICAL FIBER LINK

BACKGROUND

1. Field of the Invention

The present invention relates to the field of laser beam delivery systems, particularly to laser beam endoscopic focusing guide for use in laser surgery.

2. Description of Prior Art

At the present time laser techniques find increasing medical applications, in particular in laser surgery. To operate with a laser, a laser beam should be delivered to the operation site and converted into other forms of energy, such as heat or acoustic energy which is concentrated within a specific volume. However, operation sites usually are located remotely from the source of laser energy and are very often poorly accessible.

Optical systems used for delivering laser energy to the operation or treatment site are known as laser beam delivery systems. In case the laser operates in the visible wavelength range, it can be delivered through an optical fiber link. For surgical applications the optical fiber link is inserted, together with other surgical supplements, into a protective guiding tube which is known as an endoscopic tube.

An optical fiber or an optical fiber link normally consists of a central core portion made of a transparent, low-energy-loss material with a high refractive index, an intermediate layer known as cladding, which is made of a material having a refractive index lower than that of the core, and an outer or protective layer which is known as buffer, and which can be made of various materials, e.g., of a plastic. Light is propagated through such a fiber optical link due to well-known multiple total internal reflections. There is no leakage of light energy through the walls of the core to the outside because the core is made of a material having a higher refractive index than the outer layer.

In order to ensure propagation of the light through the optical fiber, it must be injected into the optical fiber under an incident angle, known as an acceptance angle. The acceptance angle should not exceed a predetermined threshold value, known as a critical angle. If this value is exceeded, the light will leak through the walls of the core to the outside.

Once the light is injected into the inlet end of the optical fiber at a predetermined critical angle, it will emerge, after multiple reflection from the core walls, from the outlet end face of the optical fiber at the same angle in the form of a diverging beam.

It is obvious that the energy density of the emerging light will have a maximum value at the very end of the optical fiber. Beyond the end face, the light's energy density will quickly dissipate.

For better understanding the objects and principle of the present invention, several examples of fiber optic laser techniques in surgery will be considered with reference to the principle of distribution of laser energy over the operation site.

Let us consider the case when an optic fiber is used for an operation such as thermal treatment, e.g., in dermatology, or for ablation, e.g., in surgery. Ablation is a removal of a part, such as a tumor. In order to remove a tumor by a laser beam, the tumor must be heated to a vaporization point for removing its substance by evaporation. However, when the tumor is heated, a portion of heat and light energy penetrates the surrounding healthy tissue and creates necrosis, i.e., tissue death, in this zone.

The energy supplied to the operation site can be adjusted by changing the distance between the front end of the fiber core and the surface to be treated. When this distance is increased, the energy density is reduced, and vice-versa. However, in the case described above, i.e., for the removal of the tumor, this distance cannot be considerably reduced, as the temperature will exceed the vaporization point of the tumor substance. This will result in burning and carbonization of the tumor tissue, instead of evaporation. Thus, the adjustment of energy by changing the distance is limited.

The situation is aggravated when a tumor is located inside an organ. This is because, in the course of penetration of the laser beam toward the tumor, the beam looses a considerable part of its energy and also destroys a considerable amount of the surrounding healthy tissue.

Irrespective of whether the treated tumor is on the surface or inside the organ, the process is always accompanied by a phenomenon known as "back scattering", i.e., returning of a portion of heat energy back to the fiber core. This back scattering accelerates destruction of the core.

In some cases an optical fiber can be used as a tool for cutting tissue by placing it in direct contact with the tissue. When the fiber core is used for cutting a tissue, the fiber core is moved across the operation site in the cutting direction. Such cutting is known as a "dragging" operation. Dragging is performed, not by the entire end face of the fiber core, but rather by a hot point at its leading edge. Thus the laser beam energy is utilized with extremely low efficiency, because its major part is dissipated directly into the surrounding tissue and is not used for cutting.

In other cases, laser surgery is carried out by means of an optical fiber with a sapphire tip attached to its end. An advantage of such an instrument in comparison to the one without a sapphire tip, i.e., with a flat end, is that the sapphire tip will concentrate almost the entire energy at the point of contact with the tissue. However, an instrument of this type is efficient only for cutting and is unsuitable for operations requiring either a lower operation temperature or a larger treatment area.

Optical fibers are also used in laser angioplasty, i.e., the plastic surgery of diseased blood vessels. In laser angioplasty an optical fiber is inserted into a blood vessel, moved along the vessel, and used, e.g., for removing plaque from the inner walls of the vessel.

At the present time, however, optical fiber laser angioplasty can be carried out only in relatively short and straight vessels because existing techniques suitable for such operations allows the beam to exit only in a straight-forward direction.

In addition, when plaque areas are located asymmetrically, i.e., not opposite to each other on the inner wall of the vessel, simultaneously with the removal of a plaque area, the straight-forward beam will damage the opposite inner wall.

Thus, in laser angioplasty the laser beam's energy is used inefficiently because the laser instrument is aimed at treating lateral objects while the energy beam is aimed in a forward direction. Also, the optical fiber is located in a narrow blood vessel and therefore cannot be bent. This is because, in a bent state, an optical fiber may preserve its operation characteristics only when the radius of the curvature exceeds 3-4 cm, and this is impossible because of the limited space inside the blood vessel.

In a human body, however, none of the blood vessels is ideally straight and some of them have very intricate paths, forming V-or U-shaped configurations. In order to treat hard-to-reach areas in such vessels, the laser beam should be guidable throughout a wide range of angles. The same is true, not only for angioplasty, but also for other types of laser surgery.

A more detailed description of optical fiber laser surgery techniques is given in "Optical Fibers in Medicine" (SPIE [Society of Photographic Instrumentation Engineers] 1990), Volume MS 11, Bellingham, Wash., USA.

OBJECTS OF THE INVENTION

Accordingly, several objects of the present invention are to provide a surgical laser endoscopic focusing guide which enables the laser beam energy to be directed in the lateral direction, increases efficiency of conversion of light into thermal energy, decreases back scattering of the laser beam from the treatment area, improves accuracy of treatment, and decreases zone of necrosis formed during surgery. Further objects and advantages will become apparent from the consideration of the ensuing description and drawings.

BRIEF DESCRIPTION OF DRAWINGS

FIGS. 1 and 2—General Description of the Basic Laser Endoscopic Guide

FIG. 1 is a general view of a surgical laser endoscopic focusing guide with an adjustable optical fiber.

Figure 1:
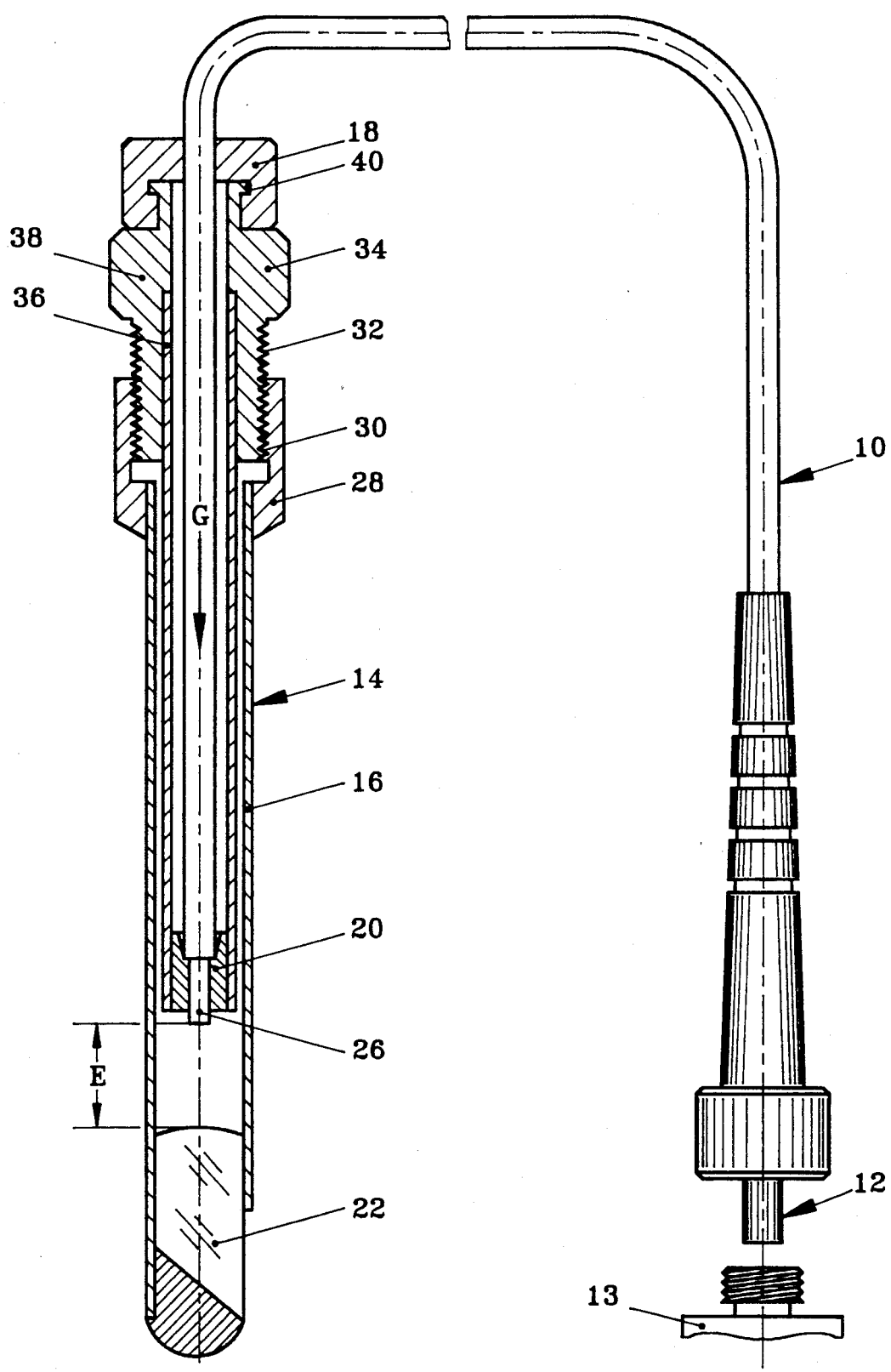
FIG. 1 is a general view of a surgical laser endoscopic focusing guide with an adjustable optical fiber, in accordance with the invention.

The apparatus consists of an optical fiber link 10, one end of which is connected to an input coupler 12 for coupling to a laser source 13, and the opposite end of which is inserted into a surgical laser beam-guiding endoscopic unit 14.

Optical fiber link 10 is a conventional optical fiber normally having the three-layer construction described above.

Unit 14 consists of an endoscopic tube 16 having on its rear end a rubber cup 18 for guiding and supporting the front end of optical fiber link 10. Inserted into a front end of endoscopic tube 16 is a fiber holder 20 that supports the front end of optical fiber link 10 in a predetermined working position with respect to an optical rodlike mirror lens 22. Lens 22 is inserted into the front end of endoscopic tube 16 and is located at a predetermined distance E from the front end face of optical fiber link 10.

The construction of rod mirror lenses and their arrangement with respect to endoscopic tubes and optical fiber link 10 will be considered in a greater detail later with reference to FIGS. 2 and 3.

A distance E between the front end of a bare fiber (which is an optical fiber link without a buffer) and lens 24 can be adjusted. This is necessary for focusing the beam (not shown), which is emitted from the endoscopic focusing guide on a target area (not shown in FIG. 1).

In order to provide the above-mentioned adjustment, an endoscopic tube 16 has a flared rear end portion 28 with an internal thread 30. Engaged with internal thread 30 is an external thread 32 of an adapter 34 which is rigidly connected to or made integrally with a tubular support 36 for a fiber holder 20 inserted into the front end of support 36. Rear end of adapter 34 is connected to a rubber cup 18A which frictionally supports optical fiber 76. Rubber cup 18 is connected to adapter 34 in such a manner that adapter 34 can rotate with respect to cup 18, but cannot be axially moved with respect to the latter. For this purpose, a shoulder 38, which is formed on the end of adapter 34, is inserted into an annular recess 40 of cup 18.

The frictional force with which optical fiber link 10 is supported by rubber cup 18 should be sufficient for feeding optical fiber link 10 in the forward direction, shown by an arrow G, when cup 18 is moved in this direction as a result of screwing adapter 34 into flared portion 28.

Figure 2:
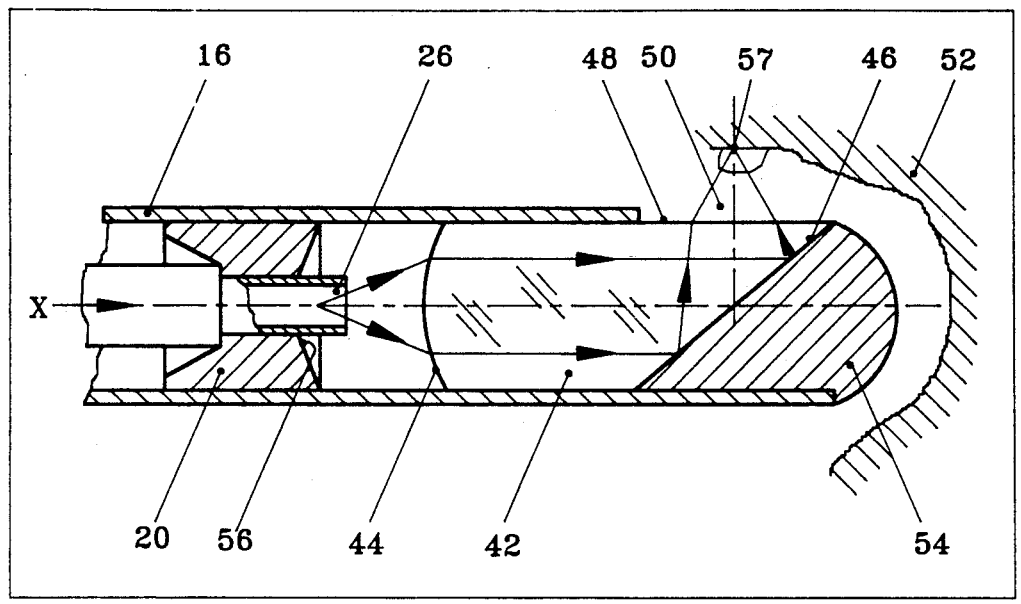
FIG. 2 is a schematic fragmentary longitudinal sectional view of a surgical laser beam-guiding part of the guide of FIG. 1 for lateral treatment.

FIG. 2 is a more detailed schematic fragmentary longitudinal sectional view of a surgical laser beam-guiding part of the apparatus of the invention for lateral treatment.

In the illustrated embodiment a mirror lens 22, which is inserted into an endoscopic tube 16, is a rod-like lens. In the context of the present invention, the term "rod-like lens" means a lens whose length is much greater than its diameter, i.e., with a ratio greater than 1. Lens 22 has a convex front surface 44 which faces a bare fiber 26, and an oblique rear reflecting mirror surface 46. Mirror surface 46 can be inclined to an optical axis X of lens 22 at an angle within a range of 3° to 160°. Lens 22 is made of a highly transparent material, such as sapphire, fused silica, etc., with a high refractive index. Mirror surface 46 is formed by a coating which has high resistance to heat. A portion of tube 16 adjacent mirror surface 46 has a window 48. This window passes a laser beam 50 reflected toward treated tissue 52 from mirror surface 46 in the direction shown by an arrow F, which is lateral to optical axis X.

A space between the front end of tube 16 and the rear end of lens 22 is filled, e.g., by a thermally resistant adhesive 54 acceptable for medical applications. Suitable adhesives are well known to the industry.

The front end of optical fiber link 10 is supported in tube 16 by fiber holder 20 which can be fixed or otherwise secured inside tube 16. Holder 20 has a central opening 56 for guiding bare fiber 26 which passes through this opening toward convex surface 44 of lens 22.

In one practical embodiment, endoscopic tube 16 had an outer diameter of 2.5 mm, the lens had the length of 25 mm, a refractive index N=1.76, a focus distance of 3 mm, and the mirror had a surface angle of 45°. Bare fiber 26 of optical fiber link 10 had a diameter of 0.6 mm, and a full beam diversion angle of 47°.

Normally, unit 14 is disposable and is supplied in a sterilized form in a sealed package.

Figure 3:
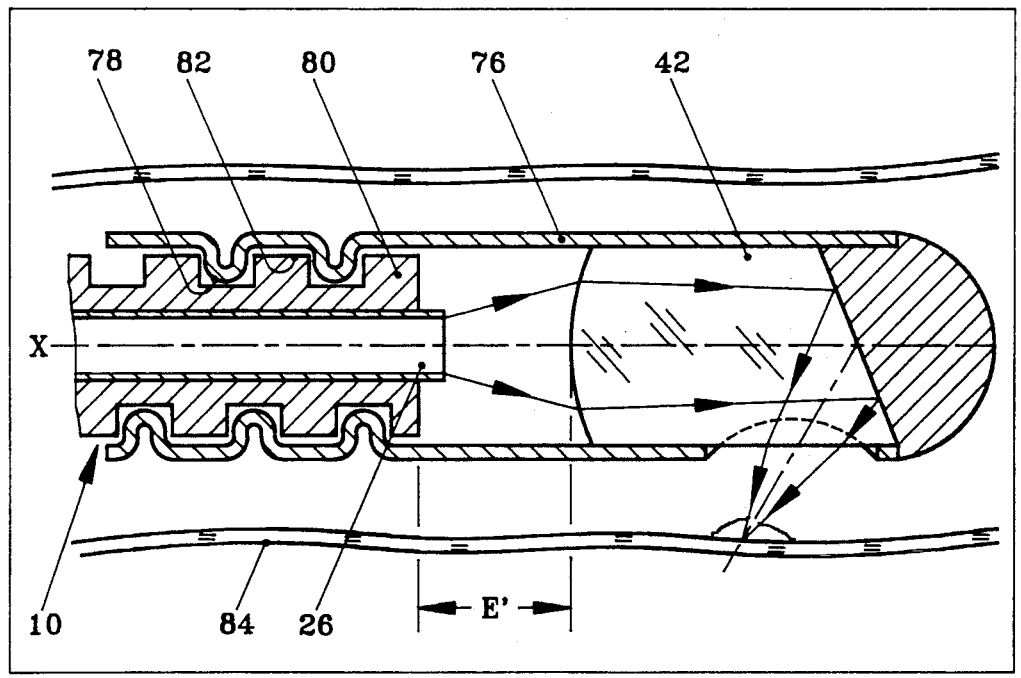
FIG. 3 is a view similar to that of FIG. 2 but with a beam focusing guide for angioplasty.

FIGS. 1 through 3—Operation of Laser Beam Focusing Guide for Ablation

Prior to laser surgery, a surgeon makes all preparations necessary for placing endoscopic tube 16 into a working position. For this purpose the surgeon inserts optical fiber link 10 into tube 16 until its front end comes into contact with fiber holder 20 and the front end of its bare fiber 26 is positioned at a distance E from the facing end of lens 22. Distance E is selected so as to provide focusing of the beam on a target area 57.

Using conventional practice, the surgeon installs unit 14 into a working position adjacent tissue 52 to be ablated and switches on laser source 13. As a result, the laser beam propagates along optical fiber link 10, is emitted from the front end of bare fiber 26 in a diverging form onto convex surface 44 of lens 22, passes through the lens body to oblique mirror surface 46, is reflected from this surface in the lateral direction F, and passes through window 48 to target area 57 of tissue 52 in the form of focusing beam 50.

Distance E, and hence focusing, can be adjusted by rotating adapter 34 which is screwed into flared portion 28 of endoscopic tube 16. As a result, adapter 34 is shifted in the direction of arrow G. Rubber cap 18 is axially moveable together with adapter 34. It also moves in the direction of arrow G, together with optical fiber link 10. As a result, distance E can be adjusted by rotating adapter 34 in a clockwise or counterclockwise direction.

FIG. 3—Beam Focusing Guide for Angioplasty

FIG. 3 is a schematic fragmentary longitudinal sectional view of another embodiment of the invention—a surgical laser beam focusing guide for lateral treatment in angioplasty.

Angioplasty requires that the endoscopic guide be inserted into narrow and curved vessels which may contain plaque. Thus during withdrawal of the device from the vessel, the lens can be disconnected and left in the vessel. Therefore a more reliable yet flexible attachment of the lens is required.

As the device of this embodiment can incorporate lenses of any type described above, only the method of attachment of the lens will be considered with reference to FIG. 3.

A lens 42 is installed in a front end of endoscopic tube made in the form of a relatively short sleeve 76. The end of sleeve 76 opposite to lens 42 has an internal thread 78.

An external or buffer layer 80 of optical fiber link 10 has an external thread 82 of the same pitch as internal thread 78 of sleeve 76. External thread 82 can be formed on the outer surface of buffer 80, e.g., by laser cutting.

Sleeve 76, which holds lens 42, is attached to optical fiber link 10 by screwing internal thread 78 of sleeve 76 onto external thread 82 of buffer 80. The same threaded connection can be used for changing a distance E' between the front end of bare fiber 26 and the facing surface of lens 42.

FIG. 3—Operation of Beam Focusing Guide for Angioplasty

The device of FIG. 3 operates in the same manner as those described above, with the exception that the treatment is carried out inside a blood vessel 84. When the device is moved along a curved vessel or extracted therefrom, the threaded connection between sleeve 76 and buffer 80 protects sleeve 76 with lens 42 from disconnection. In addition, connection of the device directly to buffer 80 ensures the flexibility required for guiding the device along curved vessels.

SUMMARY, RAMIFICATIONS, SCOPE

Thus, it has been shown that the invention provides a surgical laser endoscopic focusing guide with an optical fiber link which enables the laser beam energy to be directed in the lateral direction. It also provides such an endoscopic focusing guide which increases efficiency of conversion of light into thermal energy, decreases back scattering of the laser beam from the treatment area, improves accuracy of treatment, and decreases the zone of necrosis formed during surgery.

Although the surgical laser endoscopic focusing guide of the invention has been shown and described in the form of several specific embodiments, these embodiments, their parts, materials, and configurations have been given only as examples, and many other modifications of the apparatus are possible. For example, the connection between endoscopic tubes and optical fiber link 10 can be completed by means other than the rubber cap, or an adapter with a threaded connection. The endoscopic tube can be made of metal or plastic. Lens 22 can be fixed at the end of the endoscopic tube by means other than adhesive 54, e.g., by press-fit, caulking, etc. Although the endoscopic tube has been shown as adjustable, it also can be made in a nonadjustable form with a prefixed distance between the end of the fiber core and the end of the lens.

Therefore, the scope of the invention should be determined, not by the example given, but by the appended claims and their legal equivalents.

What we claim is:

1. A surgical laser endoscopic focusing guide apparatus for an optical fiber link having a front end, comprising:
    an endoscopic tube with a first end, a second end, an opening in a side wall of said tube, and a central axis;
    means at said first end of said tube for connecting said tube to a front end of said optical fiber link so that said central axis of said tube is coaxial with said link;
    a rod-like lens having a convex surface facing said optical fiber link and an oblique reflecting mirror surface on the end opposite to said convex surface, said reflecting mirror surface facing said side wall opening, said rod-like lens being installed adjacent to said side wall in such a location that ensures passage of said beam reflected from said mirror surface through said side wall opening at an angle to said central axis;
    means at said second end of said endoscopic tube for supporting said lens in said tube at a predetermined distance from said front end of said link; and
    means for adjusting said predetermined distance comprising a member connected to said front end of said optical fiber link and a second member connected to said second end of said tube, said first member having means for adjusting the position of said first member in the direction of said central axis with respect to said second member.

2. The guide of claim 1 wherein said oblique reflecting mirror surface is inclined at an angle within the range of 3° to 160° to said central axis.

3. The guide of claim 1 wherein said connecting means comprises a first member connected to front end of said optical fiber link and a second member connected to said second end of said tube, said first member having means for adjusting the position of said first member, in the direction of said central axis, with respect to said second member.

4. The guide of claim 3 wherein said first member comprises an external thread formed on the outer surface of said front end, said second member comprises an internal thread formed on said tube, said internal thread being engaged with said external thread.

5. The guide of claim 1 wherein said connecting means comprises an external thread formed directly on said optical link and an internal thread formed in said tube, said external and internal threads being engage and said adjustment being carried out through said engagement.

6. A surgical laser endoscopic focusing guide apparatus for an optical fiber link having a front end comprising:

an endoscopic tube with a first end, a second end, an opening in a side wall of said tube, and a central axis;

means at said first end of said tube for connecting said tube to a front end of said optical fiber link so that said central axis is coaxial with said link;

a rod-like lens having a convex surface facing said optical fiber link and an oblique reflecting mirror surface on the end of said lens opposite to said convex surface, said reflecting mirror surface facing said side wall opening, said rod-like lens being installed adjacent to said side wall in such a location that ensures passage of said beam reflected from said mirror surface through said side wall opening at an angle to said central axis;

means at said second end of said endoscopic tube for supporting said lens in said tube at a predetermined distance from said front end of said link; and means for adjusting said predetermined distance comprising a first member connected to said front end of said optical fiber link and a second member connected to said second end of said tube, said first member having means for adjusting the position of said first member in the direction of said central axis with respect to said second member, said first member comprising an external thread formed on the outer surface of said front end, said second member comprising an internal thread formed on said tube, said internal thread being engaged with said external thread.

7. The guide of claim 6 wherein said connecting means comprises an external thread formed directly on said optical link and an internal thread formed in said tube, said external and internal threads being engaged and said adjustment being carried out through said engagement.

8. The guide of claim 7 wherein said oblique reflecting mirror surface is inclined at an angle within the range of 3° to 160° to said central axis.

* * * * *